(12) United States Patent
Rink et al.

(10) Patent No.: US 10,285,758 B2
(45) Date of Patent: *May 14, 2019

(54) CONTACT LASER ABLATION OF TISSUE

(71) Applicant: Xintec Corporation, Alameda, CA (US)

(72) Inventors: John L. Rink, San Francisco, CA (US); Marilyn M. Chou, Oakland, CA (US); Mark H. K. Chim, Oakland, CA (US)

(73) Assignee: Xintec Corporation, Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/975,434

(22) Filed: Dec. 18, 2015

(65) Prior Publication Data
US 2017/0086923 A1    Mar. 30, 2017

Related U.S. Application Data

(63) Continuation of application No. 12/920,821, filed as application No. PCT/US2009/001417 on Mar. 4, 2009, now Pat. No. 9,216,059.

(Continued)

(51) Int. Cl.
*A61B 18/22* (2006.01)
*A61B 18/00* (2006.01)

(52) U.S. Cl.
CPC .... *A61B 18/22* (2013.01); *A61B 2018/00547* (2013.01); *A61B 2018/00577* (2013.01); *A61B 2018/00589* (2013.01); *A61B 2018/00625* (2013.01); *A61B 2018/00642* (2013.01); *A61B 2018/00672* (2013.01); *A61B 2018/00678* (2013.01); *A61B 2018/00708* (2013.01); *A61B 2018/00785* (2013.01); *A61B 2018/00791* (2013.01); *A61B 2018/2247* (2017.05); *A61B 2018/2255* (2013.01)

(58) Field of Classification Search
CPC ............ A61B 18/22; A61B 2018/2247; A61B 2018/2255; A61B 2018/00636; A61B 2018/00642; A61B 2018/0066; A61B 2018/00773; A61B 2018/00785; A61B 2018/00791
USPC ............ 606/3–19; 607/88, 89, 96, 100, 102; 385/12, 15; 374/100, 130–132; 356/73.1
See application file for complete search history.

(56) References Cited

U.S. PATENT DOCUMENTS 5,057,099 A * 10/1991 Rink ...................... A61B 18/20
                                                               128/898
9,216,059 B2 * 12/2015 Rink ...................... A61B 18/22

* cited by examiner

*Primary Examiner* — Ahmed M Farah
(74) *Attorney, Agent, or Firm* — GSS Law Group; Gregory S. Smith; Phillip M. Wagner

(57) ABSTRACT

Apparatus and methods are described for laser ablation of tissue. The apparatus and methods utilize a laser source coupled to a fiberoptic laser delivery device and a laser driver and control system with features for protection of the laser delivery device, the patient, the operator and other components of the laser treatment system. Advantageously, the laser source may utilize laser diodes operating at approximately 975 nm, 1470 nm, 1535 nm or 1870 nm wavelengths with a laser power output of at least 60 watts, preferably greater than 80 watts and most preferably 120-150 watts or higher. The invention, which has broad medical and industrial applications, is described in relation to a method for treatment of benign prostatic hyperplasia (BPH) by contact laser ablation of the prostate (C-LAP).

7 Claims, 12 Drawing Sheets

Related U.S. Application Data

(60) Provisional application No. 61/068,165, filed on Mar. 4, 2008.

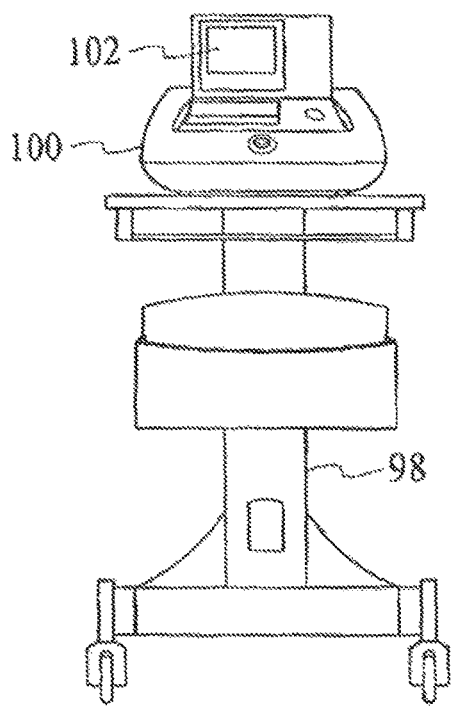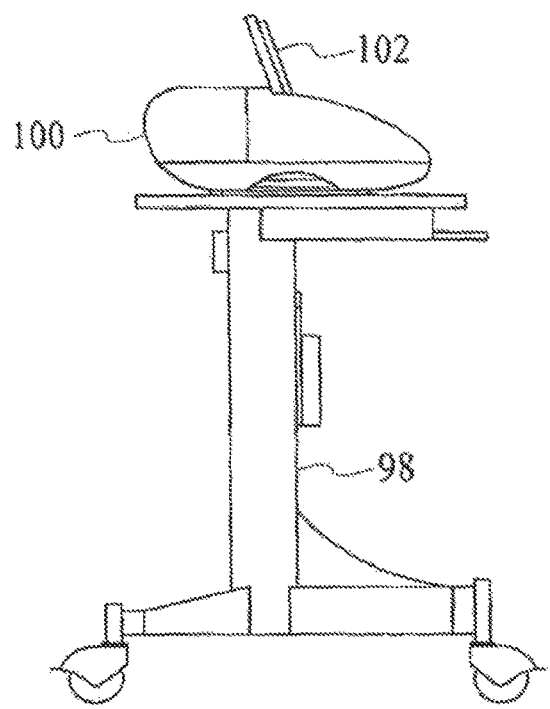
FIG.1A  FIG.1B
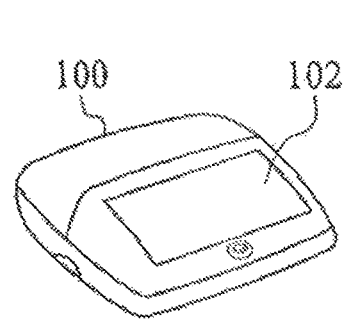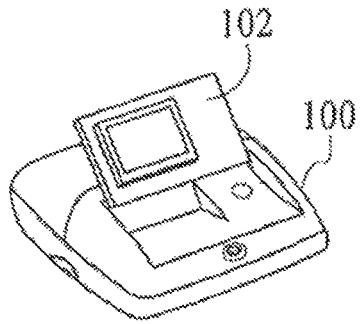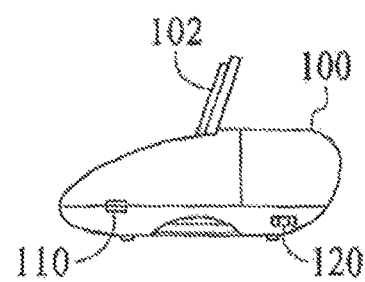
FIG.1C  FIG.1D  FIG.1E

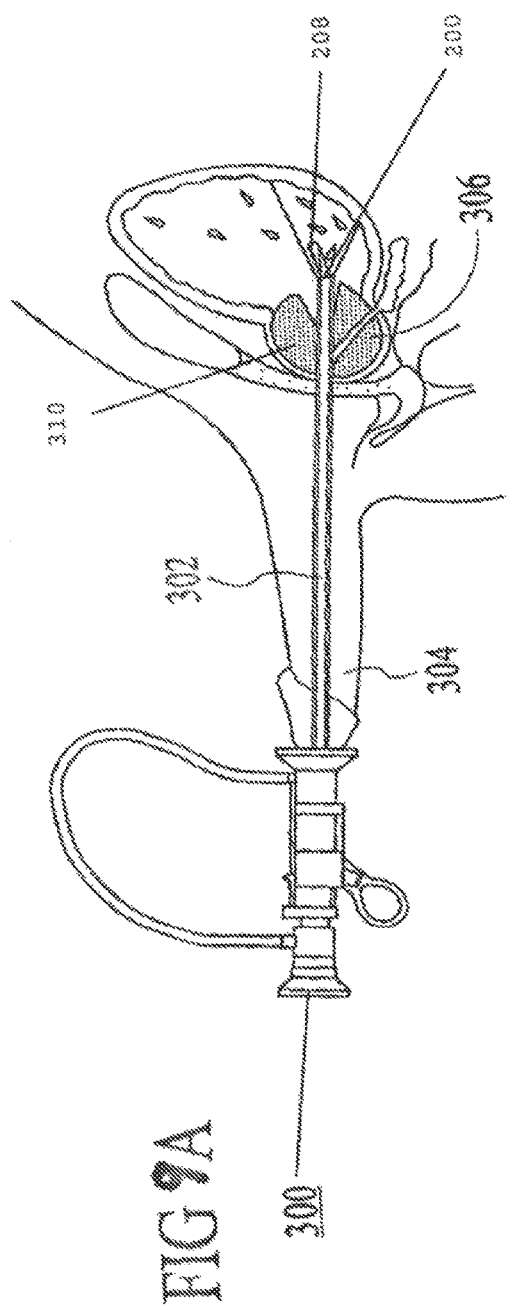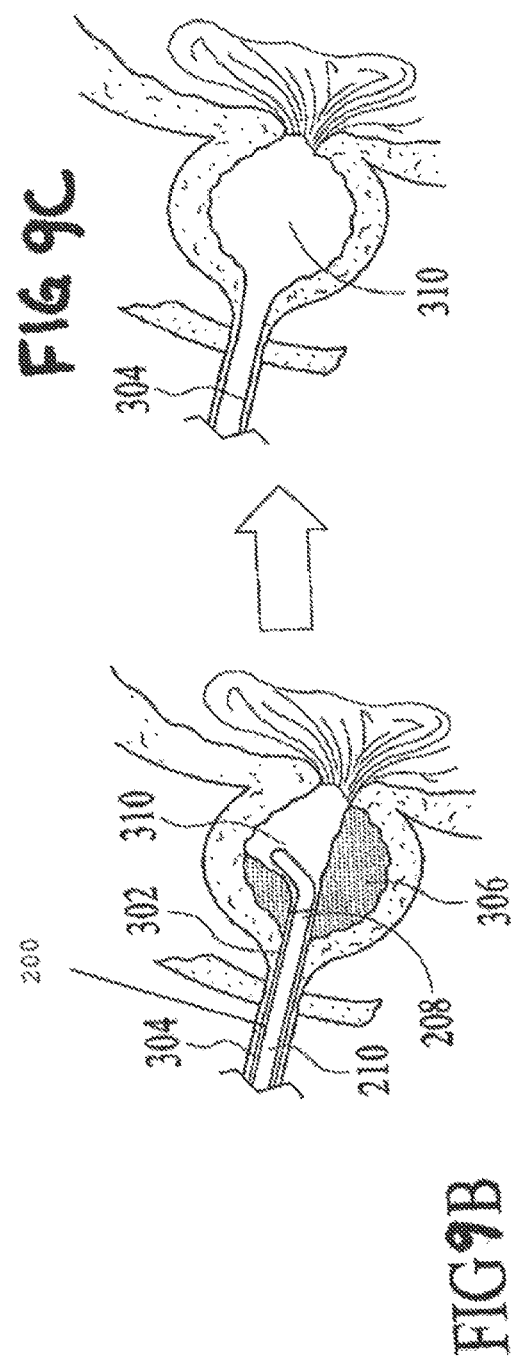

CONTACT LASER ABLATION OF TISSUE

FIELD OF THE INVENTION

The present invention relates to apparatus and methods for laser ablation of tissue. The apparatus and methods utilize a laser source coupled to a fiberoptic laser delivery device and a laser driver and control system with features for protection of the laser delivery device, the patient, the operator and other components of the laser treatment system. The invention, which has broad medical and industrial applications, is described in relation to a method for treatment of benign prostatic hyperplasia (BPH) by contact laser ablation of the prostate (C-LAP).

BACKGROUND OF THE INVENTION

The present invention has broad applications in surgery and other medical procedures for ablation, i.e. removal of obstructive or unwanted tissue, by tissue vaporization. One important application of the invention is for treatment of prostate enlargement or benign prostatic hyperplasia (BPH). BPH is a common condition in men over the age of 50 that occurs when nodular tissue from the prostate gland grows into and obstructs the urethra. BPH is characterized by difficulty urinating and a variety of other related symptoms.

Transurethral resection of the prostate (TURP) has been the most common surgical procedure for BPH. A resectoscope is inserted into the penis through the urethra and up to the prostate gland and an electrically heated wire loop is used to remove tissue from the interior of the prostate gland. TURP is considered by some to be the "gold standard" in treatment of BPH because it provides reliable symptomatic relief and can be used in large, as well as small prostate glands. However, there are significant drawbacks to the procedure. TURP is performed using spinal or general anesthesia and a 1-3 day hospital stay is generally required. A urinary catheter must be left in place for at least 1-3 days after surgery and the recovery time is typically four to six weeks. The known side effects of TURP include excessive bleeding, frequent urge to urinate, retrograde ejaculation, erection problems, painful urination (dysuria), recurring urinary tract infections, bladder neck narrowing (stricture), and blood in the urine (hematuria).

For these reasons, recent efforts have been focused on developing less invasive methods of treating BPH, including various methods of laser prostatectomy. The research goal has been to develop methods that are as effective as the "gold standard" of TURP in relieving symptoms, but are less traumatic to the patient and have fewer side effects.

One known method of performing laser prostatectomy involves using a laser for coagulation of the enlarged prostate tissue. Using a fiberoptic laser delivery device, the tissue to be removed is coagulated to kill the tissue. In one variation of this procedure, the laser energy is directed at four regions of the prostate tissue designated as the 2, 4, 8 and 10 o'clock positions. The tissue coagulation results in an immediate swelling of the surrounding tissue, therefore a catheter is allowed to remain in place for several days following the operation to allow for drainage of urine. Once the swelling subsides, the catheter is removed and over a period of several weeks the dead tissue sloughs off naturally, leaving an open passage through the urethra. Although this approach has been shown to be effective, it has the distinct disadvantage that the results are not immediate. The patient must endure the discomfort and inconvenience of having a catheter placed in the urethra for a number of days. In addition, some patients will experience continued dysuria or an inability to void after the catheter is removed.

Because of the shortcomings of the laser coagulation approach, recent efforts have been directed toward developing a method called photoselective vaporization of the prostate (PVP). Theoretically, if the enlarged prostate tissue can be completely removed at the time of treatment, then the patient should experience immediate relief from many of the symptoms. One laser that has been evaluated for this procedure is a frequency-doubled Nd:YAG laser. The 1064 nm beam of a Nd:YAG laser is directed through a nonlinear optical element, such as Potassium Titanyl Phosphate ($KTiOPO_4$ or KTP) or Potassium Dihydrogen Phosphate (KDP), which absorbs the laser radiation and reemits it at twice the frequency (that is, half the wavelength) resulting in a 532 nm visible green light beam.

The 532 nm beam of the frequency-doubled Nd:YAG laser has a high absorption in the oxyhemoglobin component of blood. Since blood is the target chromophore of the 532 nm wavelength, the first pass of the laser results in ablation and carbonization of the surface tissue. However, the underlying tissue is devascularized, resulting in reduced ablation efficiency of the 532 nm wavelength on subsequent passes of the laser. From the procedural point of view, after the first pass using a 532 nm wavelength laser for BPH, the tissue blanches and it becomes increasingly difficult to vaporize additional tissue. Completion of the procedure will require an increase in the power setting of the laser, if more power is available, or will require more procedural time at the lower tissue ablation rate. Various scientific and clinical papers have reported that, as a result of the decreased ablation efficiency, 532 nm wavelength laser systems do not perform well with large prostate glands greater than 50 gm. For example, Tugcu et al. reported that in a series of 100 patients with prostate glands ranging from 74-170 ml, a procedure time of 100-240 minutes was required for ablation using an 80 watt "KTP laser" (Urologia Internationalis 2007; 79:316-320).

The efficiency of the laser system at vaporizing tissue is also adversely affected by fowling of the fiber tip with tissue, char or other material. Once the fiber tip has been contaminated, the temperature of the fiber will quickly rise with added laser energy and thermal runaway could result in damage or destruction of the fiber. For this reason, the 532 nm wavelength laser is recommended only for non-contact vaporization of the prostate. Yet, at the same time, for effective tissue vaporization, the fiber tip must be maintained a distance of approximately 1 mm or less from the tissue surface without contacting it. In practice, this is quite difficult and requires a great deal of training and practice on the part of the surgeon.

Others have reported using a 100 watt holmium laser to treat BPH in a procedure called Holmium Laser Assisted Prostatectomy, or HoLAP. The Holmium laser at 2100 nm is highly absorbed in water, and it will ablate any tissue with even a small amount of water contained in it. Water exists in all cells. Holmium laser treatment for BPH is conducted with water as an irrigant; therefore the laser energy has to pass through water to reach its intended target. Thus, a significant amount of laser energy is lost just getting the beam to the prostate tissue. On the plus side, the extremely high absorption of the 2100 nm holmium laser energy by water means that almost all of the laser energy that reaches the tissue is used in ablation or vaporization of the tissue. Very little energy is left over to cause thermal damage and coagulation in surrounding tissue. This leads to what holmium researchers refer to as the WYSIWYG (What you see is what you get.) effect, meaning that the result seen through the cystoscope at the end of the procedure is in effect the final result because there will not be a significant amount of tissue sloughing off later due to coagulation. However, the extremely high absorption of the 2100 nm holmium laser energy at high peak power combined with the pulsed delivery also results in what some doctors have referred to as the "clam chowder" effect. The tissue gets chewed up by a multitude of tiny explosions within the tissue. After the first pass with the laser delivery device the tissue surface is pocketed with ablation craters, therefore a higher and higher percentage of the laser pulses is directed into a crater and is absorbed by the irrigation fluid so that it never reaches the tissue, which reduces ablation efficiency. In addition, while these tiny explosions are ablating tissue they are violent enough that bleeding occurs and, since there is not much tissue heating, there is not enough coagulation to control bleeding well. Additionally, while the holmium laser ablates tissue very well regardless of the presence of blood in the gland, it does so at significantly lower tissue penetration depth and lower tissue vaporization rate than the 532 nm laser, requiring even longer procedure times.

U.S. Pat. No. 5,057,099 issued Oct. 15, 1991 to John L. Rink entitled "Method for Laser Surgery", which describes a fiber tip protection system (FTPS) for use with pulsed lasers, is hereby incorporated herein by reference in its entirety. Additionally, U.S. Pat. No. 5,092,865 issued Mar. 3, 1992 to John L. Rink entitled "Optical fiber fault detector" and U.S. Pat. No. 5,269,778 issued Dec. 14, 1993 to Rink et al. entitled "Variable Pulse Width Laser and Method of Use" are hereby incorporated herein by reference in their entirety.

SUMMARY OF THE INVENTION

The present invention provides apparatus and methods for laser ablation of tissue. The apparatus includes a laser treatment system with a laser source coupled to a fiberoptic laser delivery device and a laser driver and control system for operating the laser source. The laser driver and control system implements a number of safety features for protection of the laser delivery device and other components of the laser treatment system. The laser driver and control system provides a number of advantages over the prior art. In particular, it allows the laser treatment system to be used for a method of contact laser vaporization of tissue. As noted above, many prior laser systems were limited to non-contact ablation methods because contamination of the fiberoptic laser delivery device with tissue or other matter would cause thermal runaway, quickly leading to destruction of the optical fiber. This problem is especially prevalent with high power laser sources (above about 50 watts), which is necessary for effective vaporization of tissue. The laser control system monitors the temperature and the operating condition of the fiberoptic laser delivery device and modulates the output beam to maintain the temperature below a predetermined threshold temperature or within a predetermined temperature range and alerts the user when the operating condition of the fiberoptic laser delivery device is not within a predetermined range for safe operation. The laser control system operates so as to maintain effective tissue vaporization without causing thermal runaway and damage to the fiberoptic laser delivery device. In addition, the laser driver and control system monitors other parameters of the laser treatment system for use by a proximal surface protection system, a blast shield protection system, a scope protection system, a fiber breakage detector and an ambient beam sensor.

The apparatus and methods of the present invention can be used with any type of laser that can be transmitted by a fiberoptic laser delivery device and that provides a combination of a suitable wavelength and sufficient power for tissue vaporization. Suitable laser sources include, but are not limited to: Ho:YAG laser, CTH:YAG laser, Nd:YAG laser, Er:YAG laser, frequency-doubled Nd:YAG laser, fiber lasers of various wavelengths, and direct diode lasers of various wavelengths.

One particularly preferred embodiment of the laser treatment system of the present invention utilizes a diode laser operating at a wavelength of approximately 750-2000 nm. Within this range, there are a number of commercially available laser diodes that are suitable for use in the laser treatment system, including laser diodes operating at approximately 975 nm, 1470 nm, 1535 nm and 1870 nm wavelengths (+/−20 nm). The laser treatment system will preferably be capable of a laser power output of at least 60 watts, preferably greater than 80 watts and most preferably 120-150 watts or higher. A laser treatment system specially adapted for performing contact laser tissue ablation, the VECTRA 120, been developed by Convergent Laser Technologies of Alameda, Calif. and will soon be available for clinical use.

The wavelength of a laser strongly affects the interaction of the laser beam with tissue. In particular, the specific absorption characteristics of the laser wavelength in various target chromophores present in the tissue affects the depth of penetration and the ability to coagulate and/or vaporize tissue. Examples of target chromophores that can be present in the tissue include water, hemoglobin and melanin. In addition, dyes can be added to the tissue to increase absorption of certain wavelengths. Charring of tissue generally increases the energy absorption at all wavelengths. At low power densities, lasers are typically effective at coagulating tissue, but at higher power densities, above a certain threshold level, some lasers become more effective at ablating or vaporizing tissue. A small amount of beneficial tissue coagulation typically occurs outside of the tissue vaporization region. Generally, the higher the power density of the laser beam delivered at the tissue surface, the higher the ratio of tissue vaporization to coagulation will be. The tissue vaporization threshold varies depending on the wavelength, the tissue type, the delivery method and the beam power density at the tissue surface; however it can be determined empirically for a given combination of these parameters. For contact tissue vaporization using a diode laser delivered though a fiberoptic laser delivery device as described herein for treatment of prostate tissue, reaching the tissue vaporization threshold typically requires approximately 60-80 watts of laser energy. By operating the laser above the tissue vaporization threshold, the laser treatment system of the present invention using a fiberoptic laser delivery device in tissue contact mode provides an effective treatment for benign prostatic hyperplasia by tissue vaporization.

The method of contact tissue vaporization of the present invention has a number of advantages over the prior art approaches that rely solely on non-contact tissue vaporization. The fiberoptic laser delivery device is designed to provide more contact area between the beam-emitting tip and the tissue than previous fiberoptic devices in order to maximize ablation. Direct contact allows efficient transmission of laser energy to the tissue without it being absorbed by the irrigation fluid or by turbidity in the irrigation fluid that can occur during laser ablation. The result is a marked amplification of the ablation or tissue vaporization effect of the laser and an increase in the ratio of tissue vaporization to coagulation for a given power level. Maintaining a close spacing between the laser delivery device and the tissue without inadvertent contact is quite challenging, whereas the simple pull-back motion used in the contact tissue vaporization method is easier to perform and has a much quicker learning curve for urologists who have been trained in the classic TURP technique. However, the contact tissue vaporization method places quite a bit more thermal stress and mechanical stress on the laser delivery device. It is a major inconvenience to the user to have a procedure interrupted because the laser delivery device has failed or has became too ineffective to achieve tissue vaporization. In addition, users will resist the additional cost of replacing the laser delivery device midway through a procedure. Success of the contact tissue vaporization method can thus be enhanced by using a more durable and efficient laser delivery device. More efficient laser transmission and distribution of any heat generated will reduce the thermal stress on the laser delivery device and a more durable construction will help it to resist both thermal and mechanical stresses. To this end, the present invention also provides a highly robust and durable fiberoptic laser delivery device that is constructed to minimize transmission losses and to dissipate heat buildup in the device, making it suitable for contact tissue vaporization. This more robust and durable fiberoptic laser delivery device coupled with the laser driver and control system of the invention provides a very reliable laser treatment system for contact tissue vaporization.

The invention, which has broad medical and industrial applications, is described in relation to a method for treatment of benign prostatic hyperplasia (BPH) by contact laser ablation of the prostate (C-LAP). The C-LAP procedure operates by vaporization of prostate tissue that is obstructing the lumen of the urethra and/or by debulking the tissue of the prostate to open the lumen of the urethra. The laser treatment system and the methods of contact laser tissue ablation of the present invention have numerous other applications in urology, gastroenterology, dermatology, cardiovascular treatments and many other areas of surgery and medical treatment. The laser treatment system can also be used for tissue welding and interstitial tissue treatments.

Numerous other advantages and features of the present invention will become readily apparent from the following detailed description of the invention and the embodiments thereof, from the claims and from the accompanying drawings.

BRIEF DESCRIPTION OF THE DRAWINGS

FIGS. 1A-1E show representative front and side view drawings of the diode laser system for C-LAP of the present invention, both on a mobile cart system and standing alone.

FIGS. 9A-9C illustrate representative steps for performing contact laser ablation of the prostate using the apparatus and methods of the present invention.

DETAILED DESCRIPTION OF THE INVENTION

Figure 2:
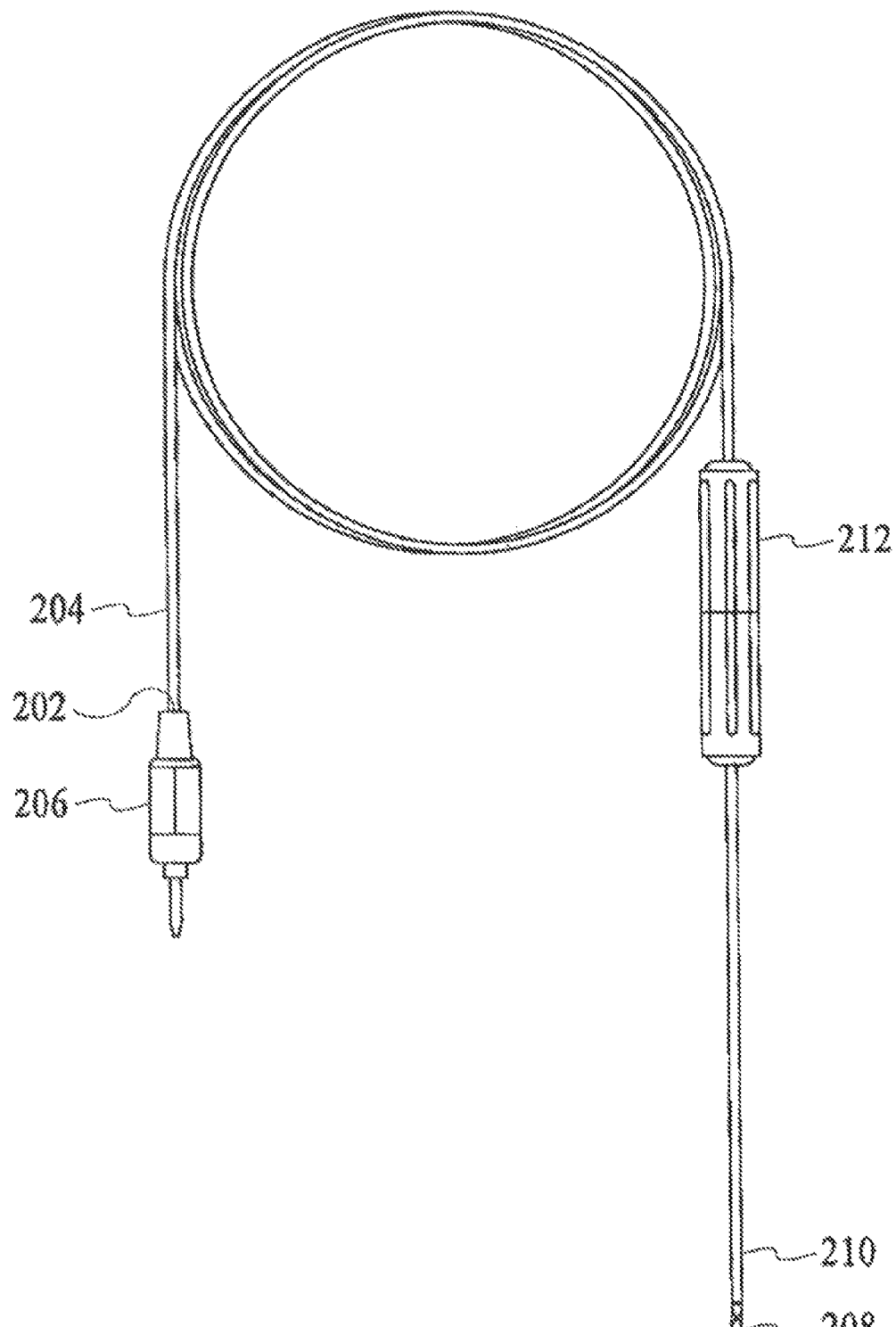
FIG. 2 is a representative schematic illustration of a fiberoptic laser delivery device for use in the method for contact tissue ablation of the present invention.

The description that follows is presented to enable one skilled in the art to make and use the present invention, and is provided in the context of a particular application and its requirements. Various modifications to the disclosed embodiments will be apparent to those skilled in the art, and the general principles discussed below may be applied to other embodiments and applications without departing from the scope and spirit of the invention. Therefore, the invention is not intended to be limited to the embodiments disclosed, but the invention is to be given the largest possible scope which is consistent with the principles and features described herein.

It will be understood that in the event parts of different embodiments have similar functions or uses, they may have been given similar or identical reference numerals and descriptions. It will be understood that such duplication of reference numerals is intended solely for efficiency and ease of understanding the present invention, and are not to be construed as limiting in any way, or as implying that the various embodiments themselves are identical.

The apparatus and methods of the present invention can be used with any type of laser that can be transmitted by a fiberoptic laser delivery device and that provides a combination of a suitable wavelength and sufficient power for tissue vaporization. Suitable laser sources include, but not limited to:

| Laser Medium | Wavelength |
|---|---|
| Ho:YAG (Holmium-doped Yttrium Aluminum Garnet) | 2100 nm |
| CTH:YAG (Chromium, Thulium, Holmium-doped Yttrium Aluminum Garnet) | 2080 nm |
| Nd:YAG (Neodymium-doped Yttrium Aluminum Garnet) | 1064 nm |
| Er:YAG (Erbium-doped Yttrium Aluminum Garnet) | 2940 nm |
| Frequency-doubled Nd:YAG laser | 532 nm |
| Diode lasers | 750-2000 nm |
| Fiber Lasers | 1000-3000 nm |

In one particularly preferred embodiment, the laser treatment system of the present invention utilizes a diode laser operating at a wavelength of approximately 750-2000 nm. Within this range, there are a number of laser diodes currently available that are suitable for use in the laser treatment system, including laser diodes operating at approximately 975 nm, 1470 nm, 1535 nm and 1870 nm wavelengths (+/−20 nm). The laser treatment system will preferably be capable of a laser power output of at least 60 watts, preferably greater than 80 watts and most preferably 120-150 watts or higher. A laser treatment system specially adapted for performing contact laser tissue ablation, the VECTRA 120, been developed by Convergent Laser Technologies of Alameda, Calif. and will soon be available for clinical use.

The choice of which laser to use in the laser treatment system of the present invention depends on a combination of technical, clinical and economic factors. The output beam of the 1535 nm (+/−20 nm) wavelength laser diode has high absorption in tissue due to a local maximum in the absorption spectrum of water, resulting in a relatively low tissue penetration and a very good ratio of tissue vaporization to coagulation above the vaporization threshold. The output beam of the 1870 nm (+/−20 nm) wavelength laser diode has nearly identical absorption in water and in tissue, but at a somewhat higher cost. The output beam of the 1470 nm (+/−20 nm) wavelength laser diode has very high absorption in tissue due to another local maximum in the absorption spectrum of water, resulting in a relatively low tissue penetration and a very good ratio of tissue vaporization to coagulation above the vaporization threshold, but at a significantly higher cost. However, new manufacturing technology and/or market forces could bring the price down to make one of these an attractive alternative to use in the laser treatment system. The 975 nm (+/−20 nm) laser diode is currently the lowest cost option capable of producing the necessary output power for effective tissue vaporization. The 975 nm wavelength output beam has good absorption in water, hemoglobin and melanin, resulting in controlled tissue penetration and a good ratio of tissue vaporization to coagulation above the vaporization threshold. This combination of features makes it another attractive alternative to use in the laser treatment system.

Fiber lasers provide a highly collimated output beam and therefore high power density, which is very beneficial for tissue vaporization. The output beam of the 1940 nm (+/−20 nm) fiber laser is also highly absorbed in water and therefore tissue. Currently, fiber laser technology is very expensive, but as the cost comes down this could be another attractive alternative to use in the laser treatment system.

For all of the wavelengths mentioned, the contact tissue vaporization method described herein enhances the effectiveness for tissue vaporization. The initial charring or carbonization of tissue increases light absorption at all wavelengths, which also enhances the effectiveness for tissue vaporization.

The laser treatment system of the present invention may also utilize two or more wavelengths of laser energy in combination.

FIGS. 1A-1E show representative front and side view drawings of the diode laser system 100, both on a mobile cart system 98 and standing alone. One of the advantages of the diode laser system 100 for performing contact tissue ablation is that it provides effective tissue vaporization throughout the procedure when it is operated at a power level above the tissue vaporization threshold. Higher tissue removal efficiency will result in shorter procedure time. Additionally, the contact tissue ablation method of the present invention causes no bleeding because there is a small amount of beneficial tissue coagulation that occurs outside of the tissue vaporization region. The contact tissue ablation method is particularly adaptable to treatment of BPH where these factors combine to provide immediate and effective relief of symptoms in BPH with a low incidence of undesirable side effects.

The diode laser system 100 is small, compact, portable and at only about 60 pounds, weighs a fraction of what a typical laser of comparable output power weighs. The diode laser system 100 in its current configuration is about 19"W× 26"L×13"H. In a preferred embodiment, a rolling cart 98 makes it convenient to roll the laser 100 from place to place, as may be desired. Preferably, the diode laser system 100 contains an LCD display or other graphical user interface portion 102 for displaying operating parameters and accepting user commands, etc. In a preferred embodiment, the graphical user interface 102 can be folded closed for storage or transport, as shown in FIG. 1C, or raised into an operating and viewing position, as shown in the other figures. A laser connector port 110 is adapted for receiving any suitable connector for coupling the laser energy created by the diode laser system 100 to a fiberoptic laser delivery device 200, such as shown in FIG. 2.

Due to its efficient operation, the diode laser system 100 has very low electrical power requirements compared to other laser systems of comparable output power. Consequently, it can be powered from a standard 100-250 volt, single phase 50/60 Hz AC electric power outlet, although it could readily be adapted to be used with other AC or DC power sources. Depending on local safety regulations, the diode laser system 100 may utilize a hospital-style locking power plug. Typically, there is no external cooling required for the diode laser system 100.

FIG. 2 is a representative schematic illustration of a fiberoptic laser delivery device 200 for use in the method for contact tissue ablation of the present invention. The fiberoptic laser delivery device 200 utilizes an optical fiber 204, which is preferably constructed with a fused silica or quartz glass core, surrounded by a glass or plastic cladding and a protective plastic jacket. At the proximal or receiving end 202 of the optical fiber 204 there is a releasable optical fiber connector 206, typically an SMA or STC connector, which are standard in the industry. Alternatively a proprietary connector may be used. The optical fiber 204 is provided with a beam-emitting tip 208 located proximate the distal end 210 of the fiber 204, which may be configured as a straight tip, a bent tip or an angle-firing tip.

Also shown is a handle or positioning apparatus 212 for use when the device is inserted through the lumen of a viewing scope or working endoscope for certain types of procedures. The distance through which the beam-emitting tip 208 is inserted into a cannula or channel of an endoscope can be adjusted and precisely positioned by the surgeon during a surgical operation. It can also serve as a handle or gripping system 212 for the fiber 204 in microprocessor based automated procedures. One such apparatus 212 would be made of two sections which can be screwed together to tighten around the jacket of the optical fiber or loosened for axial repositioning with a slight twist.

In one particularly preferred embodiment, the fiberoptic laser delivery device 200 includes a data recording device for recording data related to a procedure performed using the device 200. The data recording device may be a flash memory chip or the like and may be housed in the connector 206 at the proximal end of the optical fiber. One or more electrical connections on the connector 206 allow the data recording device to communicate with the laser system. The data recording device is preferably configured to record the date and time of the procedure, total energy laser used, error code logs from the laser, preventive maintenance logs from the laser, and the number of cases the laser has been used in. The data recording device allows better communication between the user and the manufacturer or distributor. The fiberoptic laser delivery device 200 or at least the connector 206 with the data recording device can be returned to the manufacturer or distributor to download the recorded data. The information gathered can be used to maintain inventories of fiberoptic laser delivery devices 200 and other accessories or consumables and to schedule laser system repairs and maintenance. The data recording device can also be used to facilitate a per case pricing program for the laser treatment system and/or the fiberoptic laser delivery devices 200 and other accessories or consumables. In a per case pricing program, the data recording device can be used to determine and/or to corroborate how many fiberoptic laser delivery devices 200 have been used in a given procedure. Based on this information, users can receive a refund or replacement of a fiberoptic laser delivery device 200 when more than one device was required for a given procedure.

Figure 3:
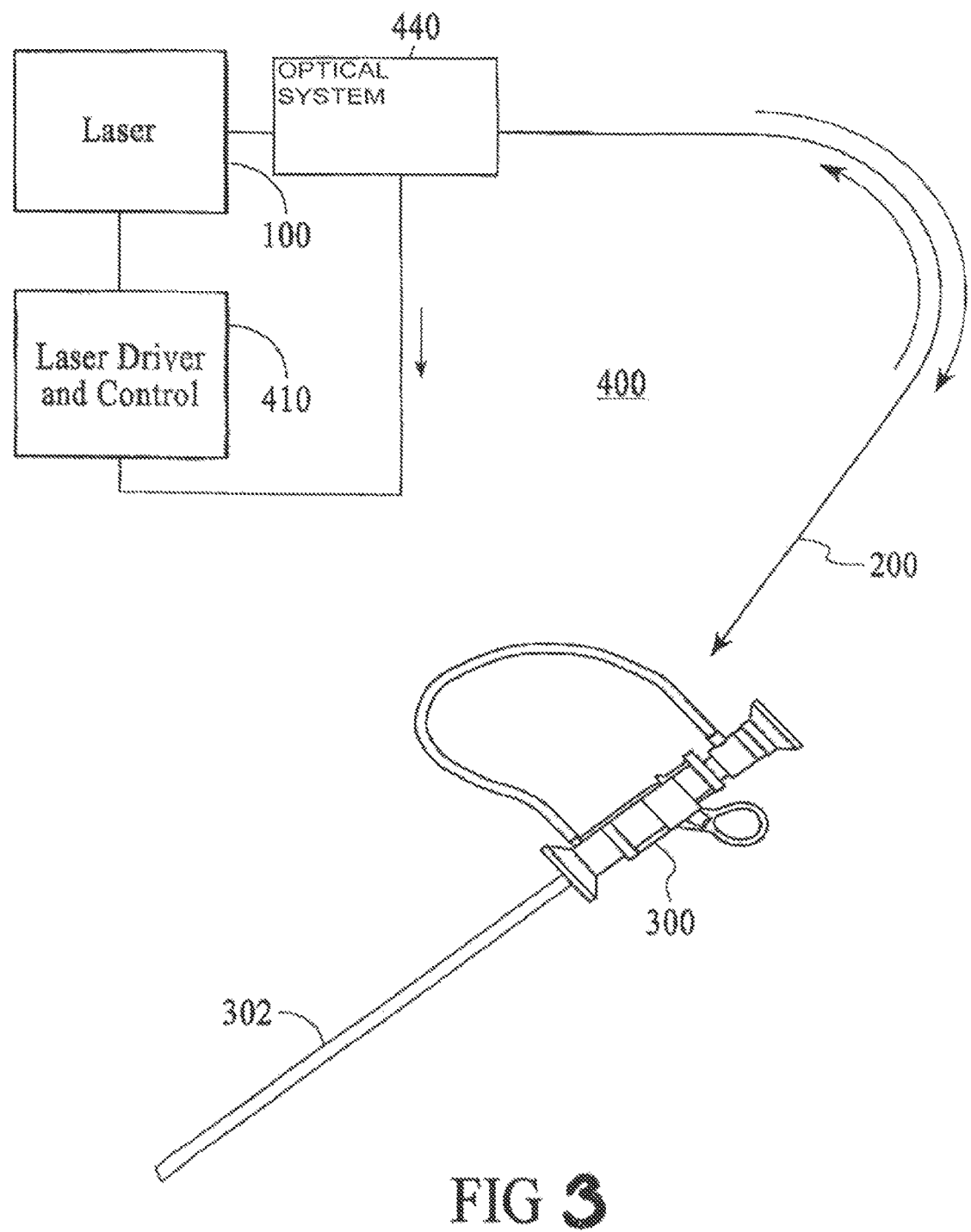
FIG. 3 is a representative schematic drawing showing a functional block diagram of the method and apparatus of the present invention for performing contact laser tissue ablation.

FIG. 3 is a representative schematic drawing showing a functional block diagram 400 of the laser treatment system of the present invention configured for contact laser ablation of tissue. The laser treatment system includes a laser source 100 that produces an output beam, which is directed through an optical system 440. The optical system 440 processes the output beam and delivers it to a fiberoptic laser delivery system 200 through a coupling device 430. The coupling device 430 is typically an SMA or STC releasable connector. The fiberoptic delivery system 200 conducts the laser energy to a beam-emitting tip 208. In addition, the optical system 440 provides feedback signals that are directed to the laser driver and control system 410, which is used to control the laser source 100.

When the laser treatment system is configured for contact laser ablation of the prostate (C-LAP), it will typically utilize a cystoscope or resectoscope 300 for visualizing the procedure. The tubular insertion portion 302 of the cystoscope 300 is placed in the urethra and the fiberoptic delivery system 200 is inserted through a working channel in the cystoscope 300.

Figure 4A:
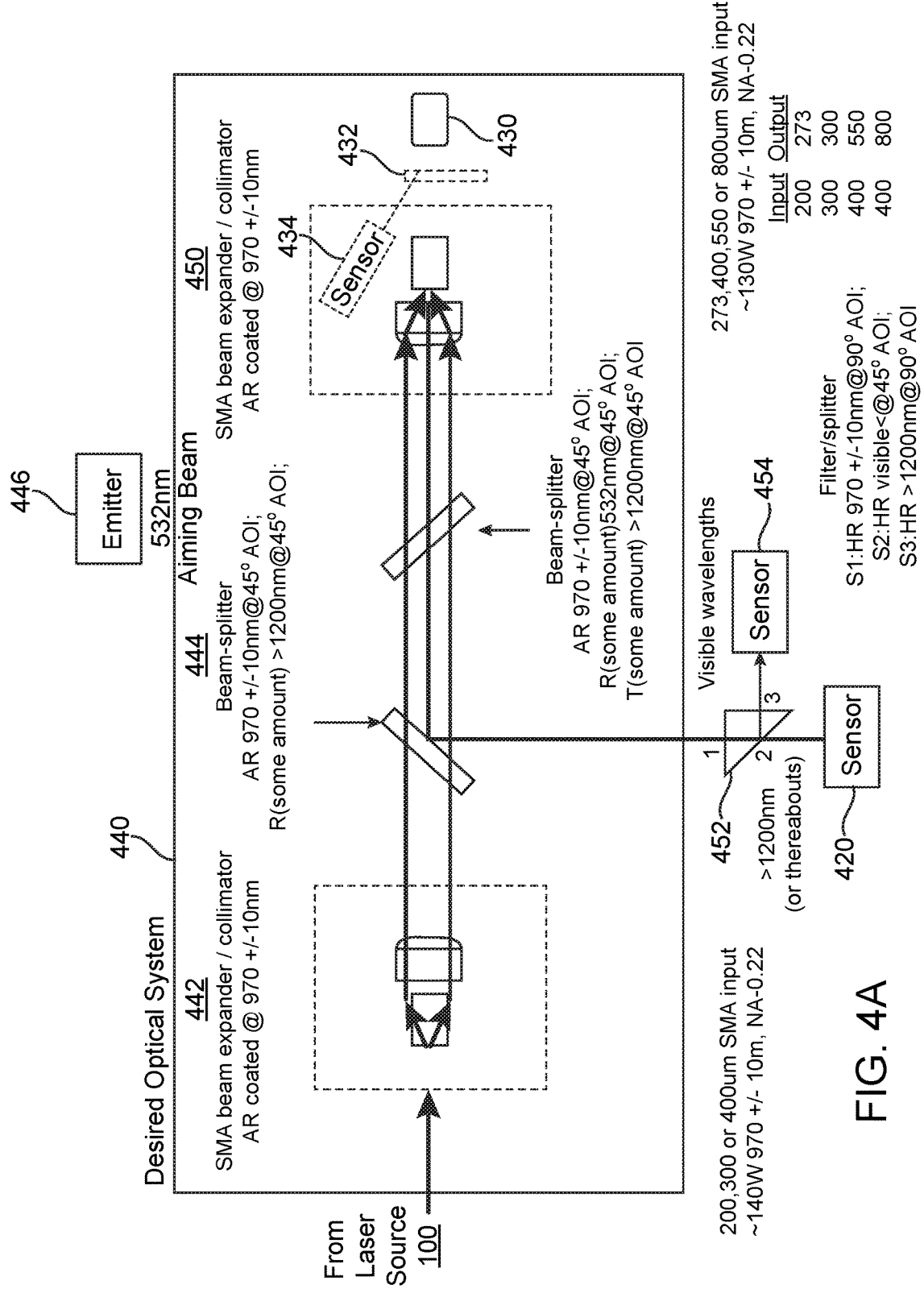
FIG. 4A is a schematic diagram of an optical system for use in the present invention.

FIG. 4A is a schematic diagram of the optical system 440 shown in FIG. 3. The configuration of the optical system 440 shown is given as an example; one of ordinary skill in the art will recognize that variations can be made to the configuration for accomplishing the intended outcome. The output beam from the laser source 100 enters the optical system 440 on the left of the diagram and passes through a beam expander/collimator 442. The optical components of the beam expander/collimator 442 preferably have an antireflective coating to maximize transmission at the laser output wavelength. The expanded and collimated beam then passes through a beam-splitter 444 positioned at an angle to the beam. The beam-splitter 444 preferably has an antireflective coating to maximize transmission at the laser output wavelength at the angle of incidence and the distal surface (right side in the diagram) will also have a reflective coating for wavelengths above 1200 nm at the angle of incidence. The beam then passes through a beam-combiner 448 and the laser output beam is combined with an aiming beam from an emitter 446 that emits a beam of visible light, for example, a low power 532 nm (green) diode pumped solid state (DPSS) laser. The beam-combiner 448 preferably has an antireflective coating to maximize transmission at the laser output wavelength at the angle of incidence and the distal surface (right side in the diagram) will also have a reflective coating for the wavelength of the aiming beam (e.g. 532 nm) at the angle of incidence. The beam-combiner 448 will also be at least partially transmissive of wavelengths above 1200 nm at the angle of incidence, which may also be accomplished with an antireflective coating if required. The combined beams pass through a beam expander/collimator 450, reversed to compress the beams and focus them on the proximal end 202 of the optical fiber 204. The optical components of the beam expander/collimator 450 preferably have an antireflective coating to maximize transmission at the laser output wavelength and are at least partially transmissive of the 532 nm wavelength and wavelengths above 1200 nm.

Light returning from the proximal end 202 of the optical fiber 204 passes in the reverse direction through the beam expander/collimator 450 and the beam-combiner 448 and is reflected by the reflective coating on the beam-splitter 444. The returning light is directed through a filter-splitter 452, which separates the visible wavelengths from the wavelengths above 1200 nm. The wavelengths above 1200 nm are directed toward an infrared sensor 420 that produces a signal indicative of the temperature of the beam-emitting tip 208, which is sent to the laser driver and control system 410. Elevated temperatures of the optical fiber proximal surface and the blast-shield, if present, will also be detected by the infrared sensor 420. The visible wavelengths are directed at a right angle toward a visible light sensor 454 that produces a signal indicative of the visible light intensity returning from the optical fiber 204, which is also sent to the laser driver and control system 410.

Figure 4B:
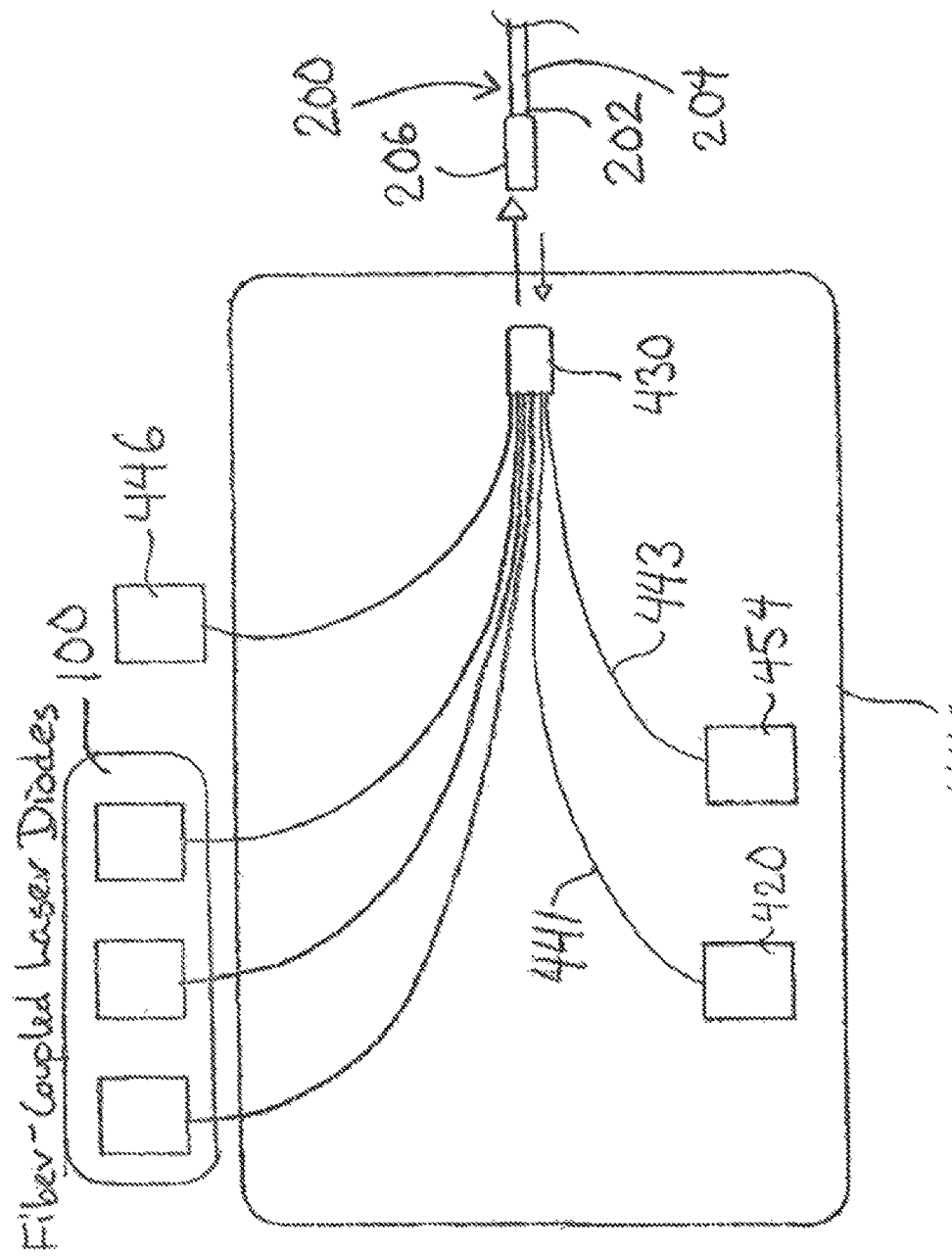
FIG. 4B is a schematic diagram of an alternate optical system for use in the present invention.

FIG. 4B is a schematic diagram of an alternate optical system 440 for use in the present invention. In this illustrative embodiment, the laser source 100 utilizes fiber-coupled laser diodes that are coupled to the proximal end 202 of the optical fiber 204. A small diameter optical fiber 441 (typically 100 microns in diameter) is coupled to the proximal end 202 of the optical fiber 204. The small diameter optical fiber 441 intercepts a portion of the light returning through the optical fiber 204 and directs it to the infrared sensor 420. A filter may be used to filter out other wavelengths and allow the infrared light to pass to the infrared sensor 420. Similarly, a second small diameter optical fiber 443 (typically 100 microns in diameter) is coupled to the proximal end 202 of the optical fiber 204. The second small diameter optical fiber 443 intercepts a portion of the light returning through the optical fiber 204 and directs it to the visible light sensor 454. A filter may be used to filter out other wavelengths and allow the visible light to pass to the visible light sensor 454.

The laser driver and control system 410 utilizes the signal from the infrared sensor 420 for the operation of a fiber tip protection system. The laser driver and control system 410 may be implemented using a microcontroller. In its current configuration, the fiber tip protection system must sample the signal from the infrared sensor 420 when the laser source 100 is off because the signal-to-noise ratio is overwhelmed by the high power of the laser's output beam when it is on. For pulsed lasers, the fiber tip protection system samples the signal from the infrared sensor 420 during the off portion of the pulse cycle. For continuous wave (CW) lasers, such as the diode lasers described above, the laser source 100 may be turned off briefly or the output beam interrupted to allow sampling of the signal from the infrared sensor 420. To accomplish this, the continuous wave laser is modulated in a pulsatile manner and the signal from the infrared sensor 420 is sampled during the off portion of the pulse cycle. In the currently preferred embodiment, the sampling occurs at a rate of approximately 100 Hz.

Alternatively, a filter may be provided to filter out other wavelengths, particularly the output wavelength of the laser source, from the infrared signal, thus allowing the continuous wave laser to be operated without interruption. In this case, the laser source can be operated in a continuous wave mode as long as the temperature threshold T1 of the fiberoptic laser delivery device 200 is not exceeded. To maintain the temperature of the fiberoptic laser delivery device 200 below T1, the laser driver and control system 410 can reduce the average power of the laser output beam by either reducing the peak power and/or by pulse modulating the beam in order to maintain the peak power density above the tissue vaporization threshold.

The magnitude of the signal from the infrared sensor 420 is indicative of the temperature of the beam-emitting tip 208 of the fiberoptic laser delivery device 200. The exact relationship between the temperature of the beam-emitting tip 208 and the magnitude of the signal from the infrared sensor 420 is somewhat variable depending on the materials and the configuration of the fiberoptic laser delivery device 200 and the materials and the configuration of the optical system 440. However, this relationship can be determined empirically for a given configuration of the laser treatment system, as can the maximum safe operating temperature or threshold temperature T1 of the fiberoptic laser delivery device 200. The fiber tip protection system operates to maintain the temperature of the beam-emitting tip 208 below the threshold temperature T1 or within a predetermined temperature range while maximizing the tissue ablation effect of the laser treatment system. The fiber tip protection system monitors the magnitude of the signal from the infrared sensor 420 and reduces the average power of the output beam from the laser source 100 when the temperature approaches the threshold temperature T1. In a preferred control scheme, this is accomplished by decreasing the duration of the laser pulses and/or by increasing the off time between pulses, while maintaining the peak power density above the tissue vaporization threshold. Optionally, the laser treatment system may be configured to determine and display the actual temperature of the beam-emitting tip 208 of the fiberoptic laser delivery device 200.

When the temperature exceeds a second threshold temperature T2, which is considered the upper limit for safe operation of the fiberoptic laser delivery device 200, the fiber tip protection system will shut off power to the laser source 100 and will alert the user. When the fiber tip protection system determines that the laser treatment system can no longer be operated for efficient tissue vaporization, e.g. when the peak power must be reduced below the tissue vaporization threshold to avoid exceeding the second threshold temperature T2, it will alert the user and give the options of changing the fiberoptic laser delivery device 200 or continuing the procedure with less efficient operation. (If the procedure is nearly finished or if the procedure can be completed with coagulation only, the user may elect to continue with the current fiberoptic laser delivery device 200.)

In an alternate control scheme, the laser driver and control system 410 can be configured to maintain the temperature of the fiberoptic laser delivery device 200 within a specified temperature range. The laser power would be adjusted up or down to keep the fiberoptic laser delivery device 200 within the specified temperature range. The laser driver and control system 410 would shut off power to the laser source 100 and alert the user of the fault if the temperature of the fiberoptic laser delivery device 200 cannot be maintained within the specified temperature range.

The laser driver and control system 410 also monitors the rate of rise, that is, the slope or derivative, of the signal from the infrared sensor 420. The rate of rise of the signal from the infrared sensor 420 is indicative of the operating condition of the fiberoptic laser delivery device 200 and in particular the beam-emitting tip 208. As the beam-emitting tip 208 becomes fouled with tissue or other debris or as microcracks develop from thermal stresses, the temperature of the beam-emitting tip 208, and hence the infrared signal, will rise more rapidly for a given level of laser power input. This information can be used in a number of ways. A threshold value can be empirically determined for the rate of rise of the signal from the infrared sensor 420 that indicates impending failure for a given configuration of the laser treatment system. The laser driver and control system 410 will be programmed to shut off power to the laser source 100 and alert the user when the rate of rise of the signal from the infrared sensor 420 approaches or exceeds the threshold value. In addition, the rate of rise of the signal from the infrared sensor 420 and the magnitude of the infrared sensor 420 can be used in an algorithm or a lookup table to determine the power level for operating the laser source 100 for optimized vaporization of tissue while avoiding thermal runaway and damage to the fiberoptic laser delivery device 200.

The infrared sensor 420 is also utilized in the function of a proximal surface protection system. The proximal end 202 of the optical fiber 204 can become contaminated or damaged during handling, installation or operation, leading to overheating of the optical fiber 204 near the proximal end 202 when the laser source 100 is operating. If left unchecked, this could result in damage to the fiberoptic laser delivery device 200 and the optical system 440 as well. The laser driver and control system 410 monitors the signal from the infrared sensor 420 and, if the signal exceeds a third temperature threshold T3, it immediately shuts off power to the laser source 100 and alerts the user. The signal for the third temperature threshold T3 can be distinguished from the signals for the first and second temperature thresholds T1, T2 because the signal strength is generally an order of magnitude higher, in part because the signal is not attenuated by passage through the optical fiber 204. Alternatively, a separate infrared sensor or other temperature sensor can be used to monitor the temperature of the proximal end 202 of the optical fiber 204.

Optionally, the optical system 440 may also include a blast shield 432, which is a sacrificial optical element interposed between the optical system 440 and proximal end 202 of the optical fiber 204. The blast shield 432 protects the components of the optical system 440 in case of thermal damage to the optical fiber 204. In a preferred embodiment, the blast shield 432 is rotatably mounted so that it can be used multiple times before it is replaced. An optional blast shield protection system includes an infrared sensor 434 or other temperature sensor that monitors the temperature of the blast shield 432. If the temperature of the blast shield 432 exceeds a predetermined threshold temperature, the laser driver and control system 410 will rotate the blast shield 432 so that a clean area of the blast shield 432 is presented to the laser beam. The laser driver and control system 410 may use the occurrence of blast shield overheating in determining the power level for operating the laser source 100. If the blast shield 432 overheats twice in close succession, the laser driver and control system 410 will shut off power to the laser source 100 and alert the user that there is a likely problem with the fiberoptic laser delivery device 200.

The signal from the visible light sensor 454, which is indicative of the visible light intensity returning from the optical fiber 204, is utilized by the laser driver and control system 410 in the function of a scope protection system. When the laser treatment system is operated through the working channel of an endoscope, such as the cystoscope 300 shown in FIG. 4, it is very important that the laser source 100 not be activated while the beam-emitting tip 208 is inside of the endoscope. This could result in significant damage to the endoscope, requiring expensive repairs to the scope. The endoscope includes an illumination system that is generally always on when the endoscope is inserted into a patient. Visible light from the endoscope's illumination system will enter the fiberoptic laser delivery device 200 through the beam-emitting tip 208 and travel back through the optical fiber 204 to the optical system 440 where it is detected by the visible light sensor 454. However, when the beam-emitting tip 208 of the fiberoptic laser delivery device 200 is withdrawn into the working channel of the endoscope, the light from the illumination system is occluded and the signal from the visible light sensor 454 is reduced. The laser driver and control system 410 monitors the signal from the visible light sensor 454 and when it drops below a certain value, it shuts off power to the laser source 100 and alerts the user.

Preferably, the laser driver and control system 410 will also be configured to determine the derivative, that is the rate of change, of the visible light returning through the optical fiber 204. As the optical fiber 204 degrades during use, the amount of visible light returning through the optical fiber 204 will gradually diminish, which should not trigger the scope protection system. The scope protection system will only shut off power to the laser source 100 if the signal from the visible light sensor 454 drops at a rate above a certain threshold, indicating that the beam-emitting tip 208 of the fiberoptic laser delivery device 200 has been withdrawn into the working channel of the endoscope.

The signal from the visible light sensor 454 is also utilized by the laser driver and control system 410 in the function of a fiber breakage detector. When the core of the optical fiber 204 breaks or burns through because of excessive mechanical or thermal stress, the signal from the visible light sensor 454 will abruptly drop because the visible light will not be coupled back across the break. When this is detected, the laser driver and control system 410 will shut off power to the laser source 100 and alert the user of the fault. Fiber breakage can generally be distinguished from withdrawing the fiberoptic laser delivery device 200 into the working channel of the endoscope by the abruptness of the change in the signal.

Optionally, the laser treatment system may be configured with the infrared sensor 420 and the visible light sensor 454 combined as a single component housing both sensors.

Preferably, the laser treatment system will also include one or more ambient beam sensors (ABS) located on the outside of the laser system enclosure, which send a signal to the laser driver and control system 410 indicating that light in the wavelength of the laser source has been detected outside of the treatment area. When this is detected, the laser driver and control system 410 will shut off power to the laser source 100 and alert the user of the fault. Preferably, the ambient beam sensors are located such that 360 degrees of the environment is monitored. This can be accomplished with a plurality of sensors mounted around the laser source or with a single sensor mounted at the highest point of the laser source, giving it a 360 degree view of the environment. The operation of the ambient beam sensors will be user controlled so that this protection system can be turned off when the laser system is used to perform surgery external to the patient. In the case of external surgery some stray laser energy is to be expected.

Another feature of the invention that can be implemented by the laser driver and control system 410 is in the nature of a heads-up display of the laser treatment system status. While operating with the laser treatment system, the surgeon will of necessity have his or her attention focused on the video display monitor of the video endoscope (or the ocular of the endoscope, if a standard optical endoscope is used) and therefore will not be able to monitor other visual displays located on the laser source or elsewhere for information about the system status. To resolve this difficulty, certain critical information about the system status can be displayed within the surgeon's visual field by modulating the aiming beam of the laser treatment system. For example, using the standard 532 nm green aiming laser 446 previously described, the aiming laser will display a continuous beam of light when all aspects of the system are operating within predetermined parameters. However, when the laser driver and control system 410 detects an approaching fault with the laser system, such as the fiberoptic laser delivery device 200 is nearing the end of its useful life, the aiming laser can switch to a slow flashing mode to alert the user of the change in status without drawing attention away from the surgical site. If the condition reaches a critical state, for example one that requires shutdown of the laser source, the aiming laser can switch to a fast blinking mode to alert the user. Information can also be displayed by using two or more colors of aiming laser. For example, a green aiming laser can be used to indicate "all systems go" and a red aiming laser can be used to indicate a system fault. Another color aiming laser, for example blue, can be used to indicate an approaching fault or other system status information. Other information and/or finer gradations in the system status can be displayed by using different flashing modes as described above or by combining or alternately flashing the different colors of aiming lasers.

Figure 5:
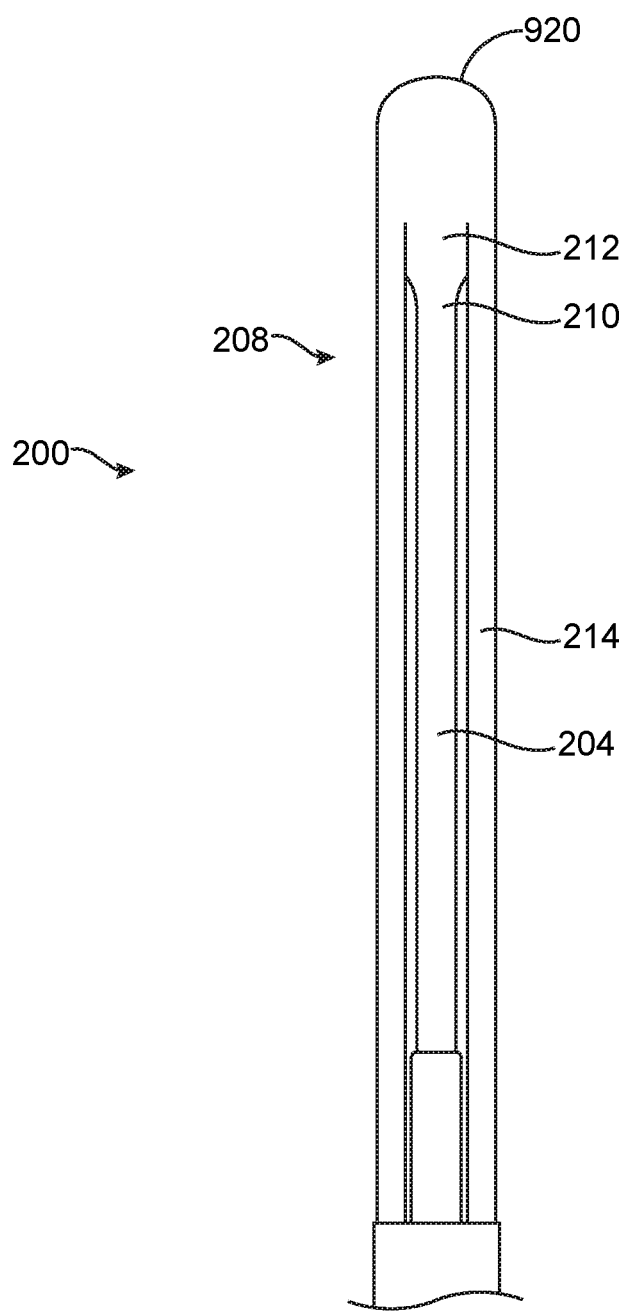
FIG. 5 is a longitudinal cross section of a straight tip fiberoptic laser delivery device with a beam-emitting distal surface.

FIG. 5 is a longitudinal cross section of a distal portion of a straight tip fiberoptic laser delivery device 200 as used in the apparatus and method of the present invention for contact laser ablation of tissue. As described above, the fiberoptic laser delivery device 200 includes a beam-emitting tip 208 located adjacent the distal end 210 of the optical fiber 204. In this embodiment, the device has a straight beam-emitting tip 208 ending in a beam-emitting distal surface 920. The cladding 918 is stripped back and the distal end 210 of the optical fiber 204, which typically has a quartz core of approximately 600 microns diameter, is fused to a larger diameter fiber tip member 212. The fiber tip member 212 may be fabricated by fusing a separate plug of quartz material to the distal end 210 of the optical fiber 204 or, more preferably, the distal end 210 may simply be melted and allowed to form into a ball or plug shape. The exterior of the fiber tip member 212 is fused to a quartz tube 214, which surrounds the fiber tip member 212. Forming the larger diameter fiber tip member 212 and fusing it to the quartz tube 214 can be accomplished in a single step, if desired. The quartz tube 214 is a hollow cylinder with an inside diameter just large enough to pass over the fiber tip member 212 during assembly and an outside diameter that is preferably approximately 2 mm. In the example shown, the quartz tube 214 is approximately 1-2 cm long. By fusing the distal end 210 of the quartz core optical fiber 204 to the fiber tip member 212 and the quartz tube 214, an optical path is created that is free of any changes in refractive index that would result in transmission losses of the laser beam. The high efficiency of laser beam transmission from this arrangement has two beneficial results: the most laser energy possible is delivered to the tissue through the beam-emitting distal surface 920 for effective tissue vaporization, and lower transmission losses minimize the heating of the beam-emitting tip 208. In addition, the expanded surface area of the beam-emitting distal surface 920 and the increased thermal mass of the beam-emitting tip 208 also contribute to reducing the temperature of the beam-emitting tip 208 during use, all of which results in a longer usable life for the fiberoptic laser delivery device 200. The expanded diameter of the beam-emitting tip 208 places more surface area in contact with the tissue, which is beneficial for tissue vaporization. Furthermore, the additional mass of the beam-emitting tip 208 provides some sacrificial material to compensate for the erosion of the beam-emitting distal surface 920, which is inevitable when operating the laser treatment system at high power in contact with tissue. The sacrificial material protects the core of the optical fiber 204 from catastrophic failure and lengthens the usable life of the fiberoptic laser delivery device 200.

The fiberoptic laser delivery device 200 can be constructed in other sizes and materials if desired, as long as the basic design considerations are adhered to. To reduce transmission losses and minimize heating of the device, the optical fiber 204 should be made of a material that efficiently transmits the chosen laser wavelength and the fiber tip member 212 and the tube 214 should be made of compatible optical materials that are fusible with the optical fiber 204 and have closely matching refractive indices. Making all of the optical components from the same material also has the effect of reducing the thermal stresses in the device because all of the components will have the same thermal expansion coefficient.

Figure 6:
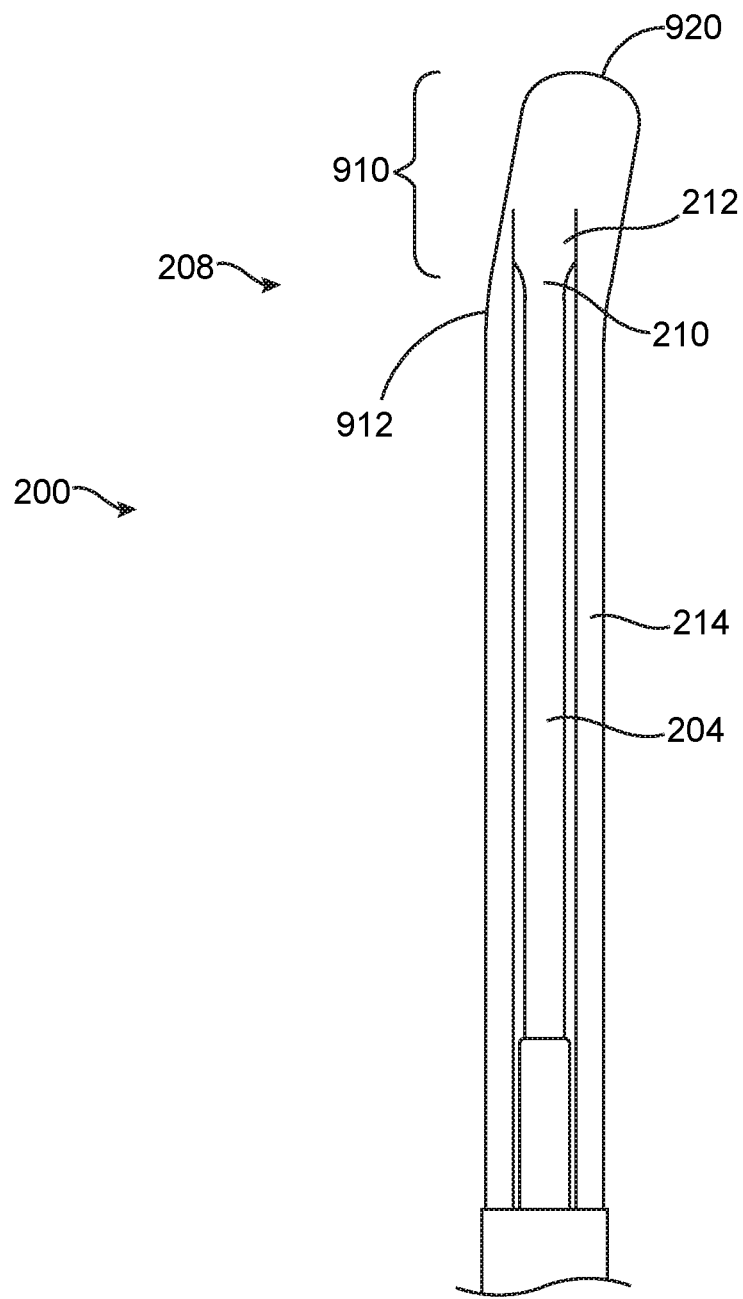
FIG. 6 is a longitudinal cross section of a bent tip fiberoptic laser delivery device with a bent portion ending in a beam-emitting distal surface.

FIG. 6 is a longitudinal cross section of a bent tip fiberoptic laser delivery device 200 for use with the laser system 100 of the present invention for contact laser ablation of tissue. This embodiment is particularly well adapted for treatment of benign prostatic hyperplasia using the C-LAP method. In this embodiment, the device has an angled beam-emitting tip 208 with an angled distal portion 910 ending in a beam-emitting distal surface 920. Similar to the straight tip embodiment described above, the distal end 210 of the optical fiber 204 is fused to a larger diameter fiber tip member 212 that has a diameter that is greater than the diameter of the optical fiber 204. The fiber tip member 212 may be fabricated by fusing a separate plug of quartz material to the distal end 210 of the optical fiber 204 or, more preferably, the distal end 210 may simply be melted and allowed to form into a ball or plug shape. The exterior of the fiber tip member 212 is fused to a quartz tube 214, which surrounds the fiber tip member 212. A bend 912 is formed in the quartz tube 214 to create the angled distal portion 910 by heating and bending the quartz tube 214 and the optical fiber 204. The angled distal portion 910 allows the user to keep the beam-emitting distal surface 920 in contact with the tissue when performing the C-LAP procedure. The angled distal portion 910 increases the surface area of the beam-emitting tip 208 in contact with the tissue.

Figure 7:
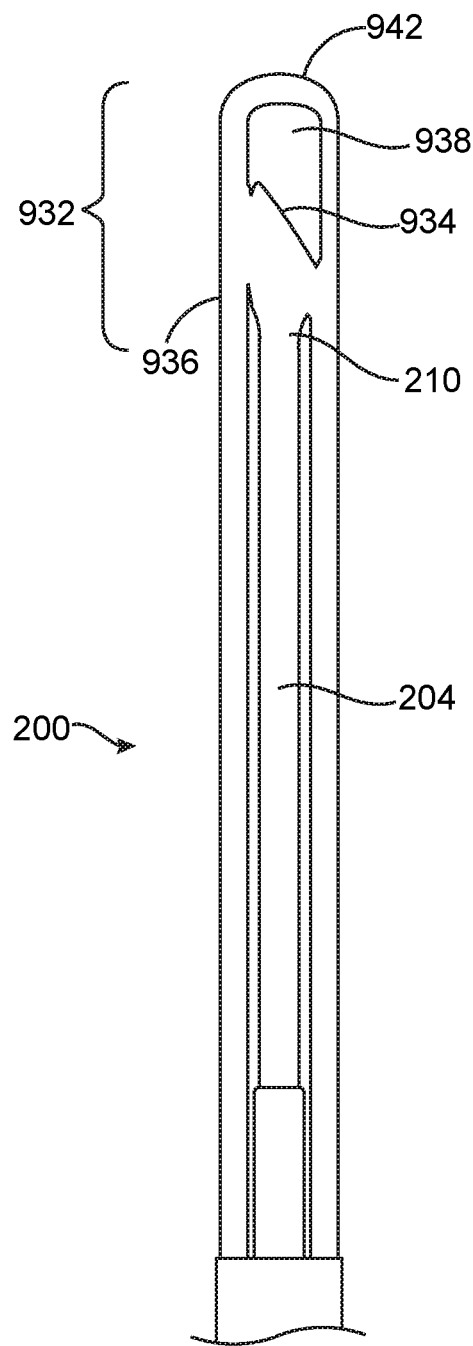
FIG. 7 is a longitudinal cross section of another fiberoptic laser delivery device having a side-firing tip with an angled reflective surface that redirects the laser beam out through a beam-emitting lateral surface.

FIG. 7 is a longitudinal cross section of another fiberoptic laser delivery device 200 for use with the laser system 100 of the present invention for tissue vaporization treatment of benign prostatic hyperplasia. In this embodiment, the device has a side-firing tip 932 with an angled reflective surface 934 that redirects the laser beam out through a beam-emitting lateral surface 936. The distal end 210 of the optical fiber 204 is fused to a larger diameter fiber tip member 212 that has a diameter that is greater than the diameter of the optical fiber 204. The fiber tip member 212 may be fabricated by fusing a separate plug of quartz material to the distal end 210 of the optical fiber 204 or, more preferably, the distal end 210 may simply be melted and allowed to form into a ball or plug shape. An angled reflective surface 934 is formed on the end of the larger diameter fiber tip member 212. This results in a larger diameter reflective surface 934 that prevents the loss of laser energy out the distal end of the side-firing tip 932 or at the acute angle where the reflective surface 934 meets the outer diameter of the fiber tip member 212. The angled reflective surface 934 may simply be a polished surface backed by a lower refractive index material, such as air, so the laser beam is redirected by total internal reflection. Alternatively, the reflective surface 934 may be formed by depositing gold, silver or another reflective coating, such as a multilayer dielectric coating, on the polished angled surface. The reflective surface 934 may be polished flat or it may be polished into a concave or convex surface for focusing or defocusing of the laser beam, as desired. The more reflective the reflective surface 934 is at the chosen wavelength, the lower the reflective losses will be and the lower the thermal stresses will be on the device 200 during use. The exterior of the fiber tip member 212 is fused to a quartz tube 214, which surrounds the fiber tip member 212. Particularly if total internal reflection is used, the distal end 942 of the quartz tube 214 is fused closed to enclose a gap 938 between the reflective surface 934 and the quartz tube 214 that is filled with air or, more preferably, a gas or gas mixture with a low index of refraction and a low coefficient of thermal expansion.

Figure 8:
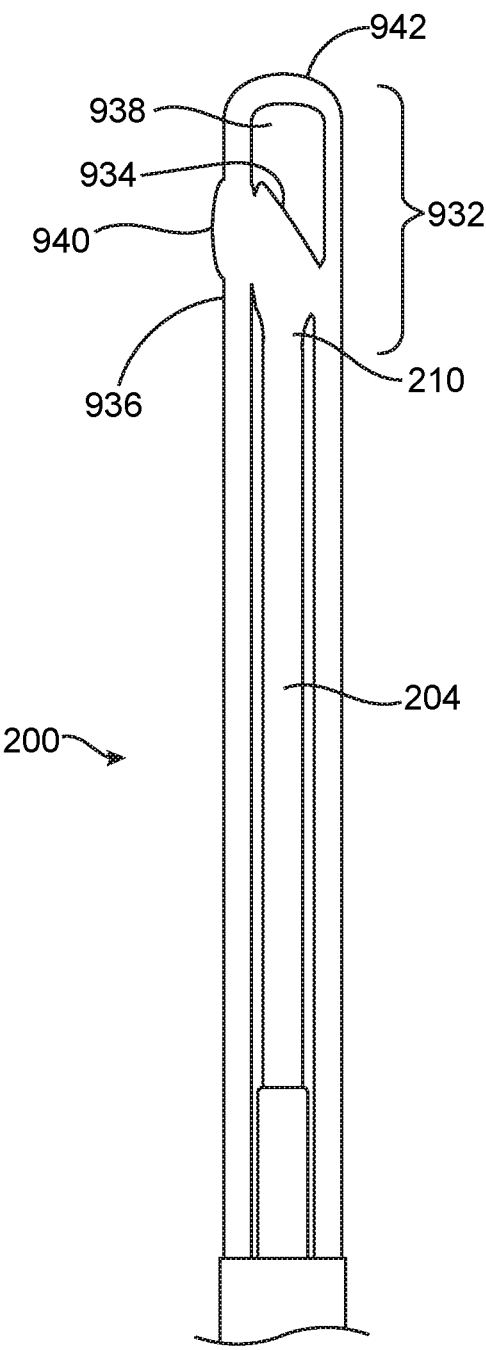
FIG. 8 is a longitudinal cross section of another fiberoptic laser delivery device having a side-firing tip with an angled reflective surface that redirects the laser beam out through a lens on the lateral surface of the device.

FIG. 8 is a longitudinal cross section of another fiberoptic laser delivery device 200 for use with the laser system 100 of the present invention for tissue vaporization treatment of benign prostatic hyperplasia. This embodiment is similar to the embodiment of FIG. 7 with a side-firing tip 932, except in this case the angled reflective surface 934 directs the laser beam out through a lens 940 on the lateral surface 936 of the device. Preferably, the lens 940 is formed of quartz and is fused directly to the lateral surface 936 of the device to minimize transmission losses. The lens 940 provides additional sacrificial material at the point of tissue contact without significantly increasing the bulk of the side-firing tip 932. Optionally, the lens 940 may be shaped to focus or defocus the output beam, as desired. Alternatively, if higher focusing power is needed, a higher refractive index material may be used for the lens 940. In this case, an anti-reflective coating may optionally be used between the lateral surface 936 of the device and the focusing lens 940 to reduce transmission losses and to reduce thermal stresses on the device in use.

The method of contact tissue vaporization of the present invention has a number of advantages over the prior art approaches that use non-contact tissue vaporization. Direct contact allows efficient transmission of laser energy to the tissue without it being absorbed by the irrigation fluid or by turbidity in the irrigation fluid that occurs during some laser ablation methods. Maintaining a close spacing between the laser delivery device and the tissue without inadvertent contact is quite challenging, whereas the simple pull-back motion used in the contact tissue vaporization method is easier to perform and has a much quicker learning curve for urologists who have been trained in the classic TURP technique. However, the contact tissue vaporization method places quite a bit more thermal stress and mechanical stress on the laser delivery device. It is a major inconvenience to the user to have a procedure interrupted because the laser delivery device has failed or has become too ineffective to achieve tissue vaporization. In addition, users will resist the additional cost of replacing the laser delivery device midway through a procedure. Success of the contact tissue vaporization method depends in large part on using a laser with the correct wavelength and power output for tissue vaporization, coupled with a more durable and efficient laser delivery device. More efficient laser transmission and distribution of any heat generated will reduce the thermal stress on the laser delivery device and a more durable construction will help it to resist both thermal and mechanical stresses. The fiber tip protection system greatly enhances the contact tissue vaporization method by prolonging the usable life of the laser delivery device while optimizing the delivery of laser energy for effective tissue vaporization.

FIGS. 9A-9C illustrate representative steps for performing contact laser ablation of the prostate using the apparatus and methods of the present invention. As shown in FIG. 9A, the tubular insertion portion 302 of a cystoscope 300 or other endoscope is introduced through the urethra 304. A working lumen in the tubular insertion portion 302 of the cystoscope 300 provides access to the enlarged prostate 310 for insertion of a fiberoptic laser delivery device 200, such as that shown in FIG. 2.

In the next step, shown in FIG. 9B, the laser source is activated to deliver laser energy through the fiberoptic laser delivery device 200 with the beam-emitting tip 208 in contact with the prostate tissue 306 that is obstructing the urethra 304. The fiberoptic laser delivery device 200 can be used to create a flow channel through the prostate gland by vaporizing tissue that is obstructing the urethra. In addition, the fiberoptic laser delivery device 200 can be used to debulk the enlarged prostate by removing additional tissue 306 leaving a fully treated, open, hollow and clear prostate portion 310. As a result, the prostate can be left fully opened, hollowed out and essentially rendered less restrictive of flow of fluids through the open prostate 310, as shown in FIG. 9C.

Figure 10A:
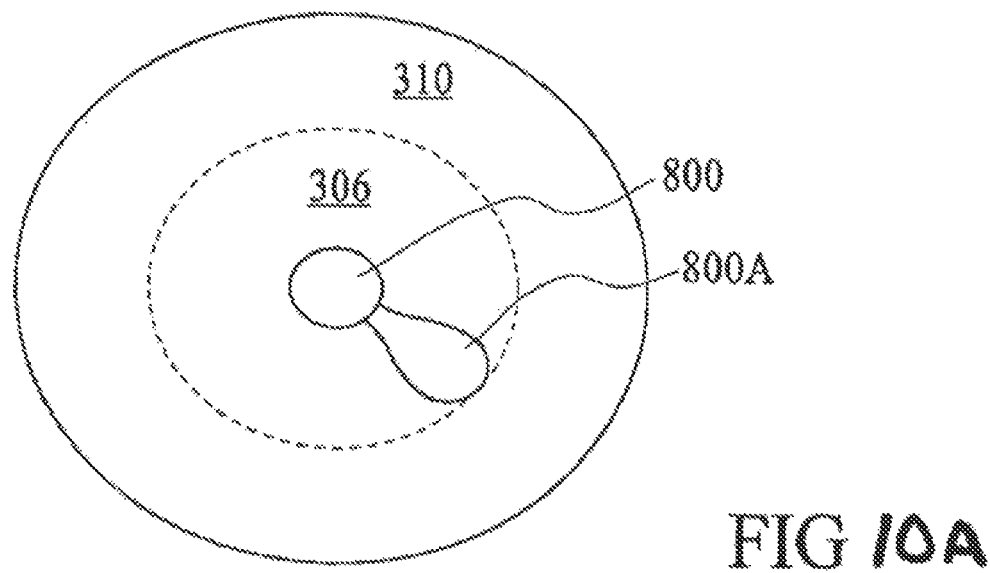
FIGS. 10A-10D illustrate an example of a method of performing C-LAP according to the present invention.

FIGS. 10A-10D illustrate an example of one preferred method of performing C-LAP according to the present invention. The fiberoptic laser delivery device 200 is advanced through the working channel of a cystoscope placed in the patient's urethra 800 and into the prostate gland, as described in connection with FIG. 9A. The beam-emitting tip 208 of the fiberoptic laser delivery device 200 is advanced past the narrowing of the urethra in the prostate gland. Then, the laser source 100 is activated and the fiberoptic laser delivery device 200 is pulled back through the area of the prostate gland to be treated with the beam-emitting tip 208 in contact with the tissue. FIG. 10A shows a cross section of the enlarged prostate gland after one pass of the fiberoptic laser delivery device 200. The laser energy has vaporized a trough 800A of prostatic tissue contacted by the beam-emitting tip 208. In addition, the laser energy has created a thin layer of beneficial tissue coagulation surrounding the trough 800A. The depth of the tissue coagulation layer will depend on the laser wavelength and power setting, as well as the configuration and condition of the beam-emitting tip 208. Generally, the laser driver and control system 410 will strive to operate the laser source 100 so as to maximize the ratio of tissue vaporization to tissue coagulation given the parameters of the user-selected power level and the operating condition of the fiberoptic laser delivery device 200.

Figure 10B:
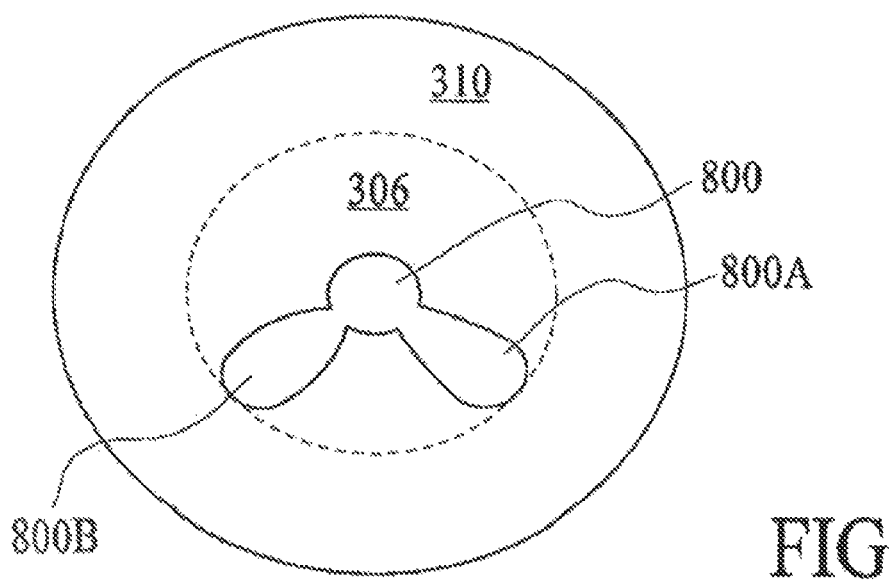
Figure 10C:
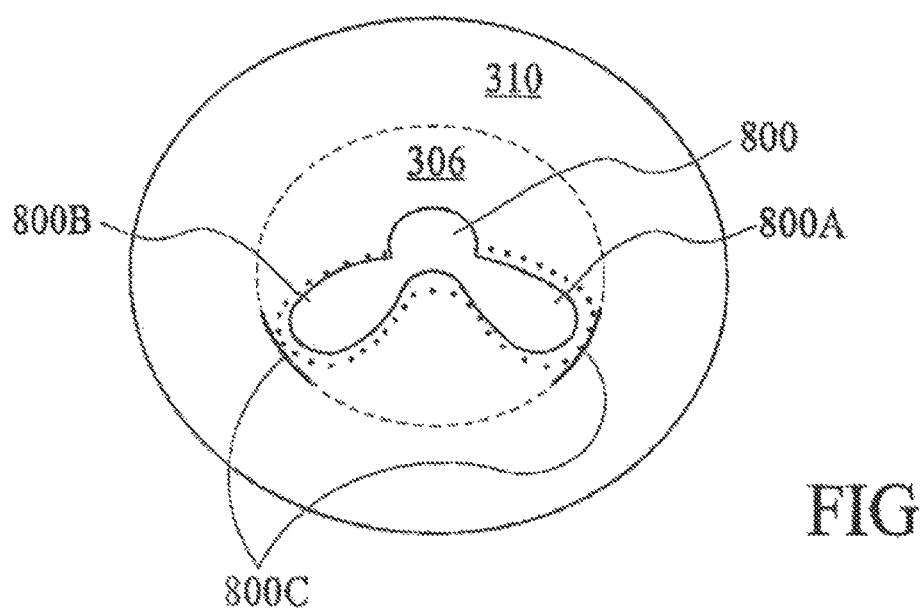

A single pass of the fiberoptic laser delivery device 200 may be enough to provide symptomatic relief in some patients, however additional passes of the device will typically be needed. The beam-emitting tip 208 of the fiberoptic laser delivery device 200 is again advanced past the narrowing of the urethra in the prostate gland, and the laser source 100 is activated while the fiberoptic laser delivery device 200 is pulled back with the beam-emitting tip 208 in contact with the tissue. FIG. 10B shows a cross section of the enlarged prostate gland after a second pass of the fiberoptic laser delivery device 200. The laser energy has vaporized a second trough 800B of prostatic tissue with a thin layer of beneficial tissue coagulation surrounding the trough 800B. The second trough 800B may be created immediately adjacent to the first trough 800A so that the two troughs are contiguous. Thus, multiple passes of the fiberoptic laser delivery device 200 can be used to create an enlarged passage through the prostate gland.

Alternatively, the second trough 800B may be spaced apart from the first trough 800A, as shown in FIG. 10B. Depending on the laser wavelength and other parameters, much of the tissue between the two troughs may be coagulated, as illustrated in FIG. 8C. The zones of coagulation 800C are beneficial in preventing internal bleeding from the inside of the healthy remaining prostatic tissue 310. The zones of coagulation 800C are essentially cauterized surfaces extending a shallow layer into the prostate, but not deep enough to interfere with the viability and normal function of the prostate 310.

Figure 10D:
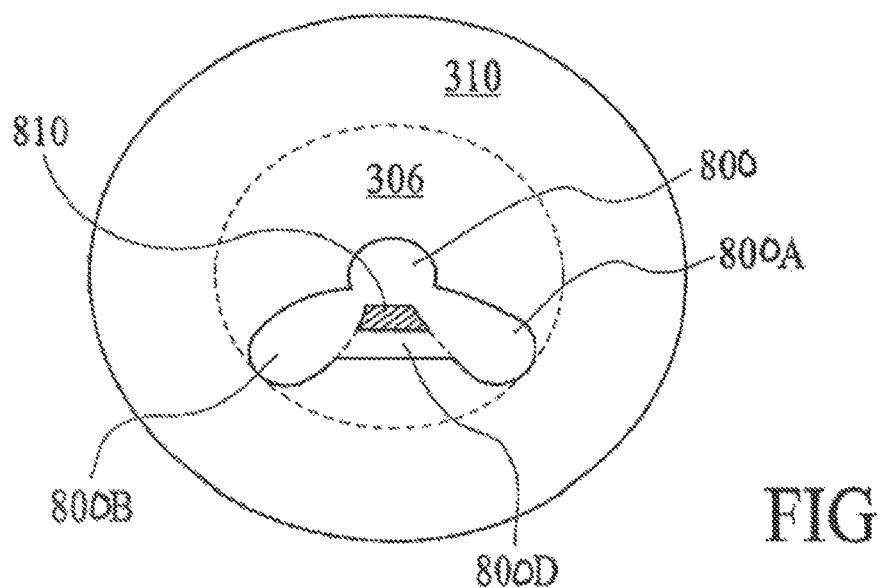

The coagulated tissue may simply be left to slough off after surgery, which further enlarges the passage through the prostate gland. However, for immediate symptomatic relief, it would be preferably to remove the tissue between the two troughs at the time of surgery. In one variation of this method which is describe further below, this can be accomplished by combining the C-LAP procedure with a TURP procedure to remove the coagulated tissue. The tissue between the two troughs can also be efficiently removed with a third pass of the fiberoptic laser delivery device 200, as illustrated in FIG. 10D. The fiberoptic laser delivery device 200 is positioned within one of the troughs previously created at the base or deepest point of the trough with the beam-emitting tip 208 oriented toward the other trough. The laser source 100 is activated while the fiberoptic laser delivery device 200 is pulled back with the beam-emitting tip 208 in contact with the tissue. This vaporizes a trough 800D that joins the base of the first trough 800A with the base of the second trough 800B. At the same time, it excises a portion of the tissue 810 between the two troughs. The result is a much more efficient rate of tissue removal using the fiberoptic laser delivery device 200. This provides the additional benefit of shortening the duration of the C-LAP procedure. This benefits the health care provider by making more efficient use of hospital facilities and staff and it benefits the patient by reducing anesthesia time while simultaneously providing more effective symptomatic relief. If desired, a fourth and a fifth pass of the fiberoptic laser delivery device 200 can be used to excise an additional portion of tissue. These steps can be repeated as many times as necessary for debulking especially large prostate glands.

Figure 11:
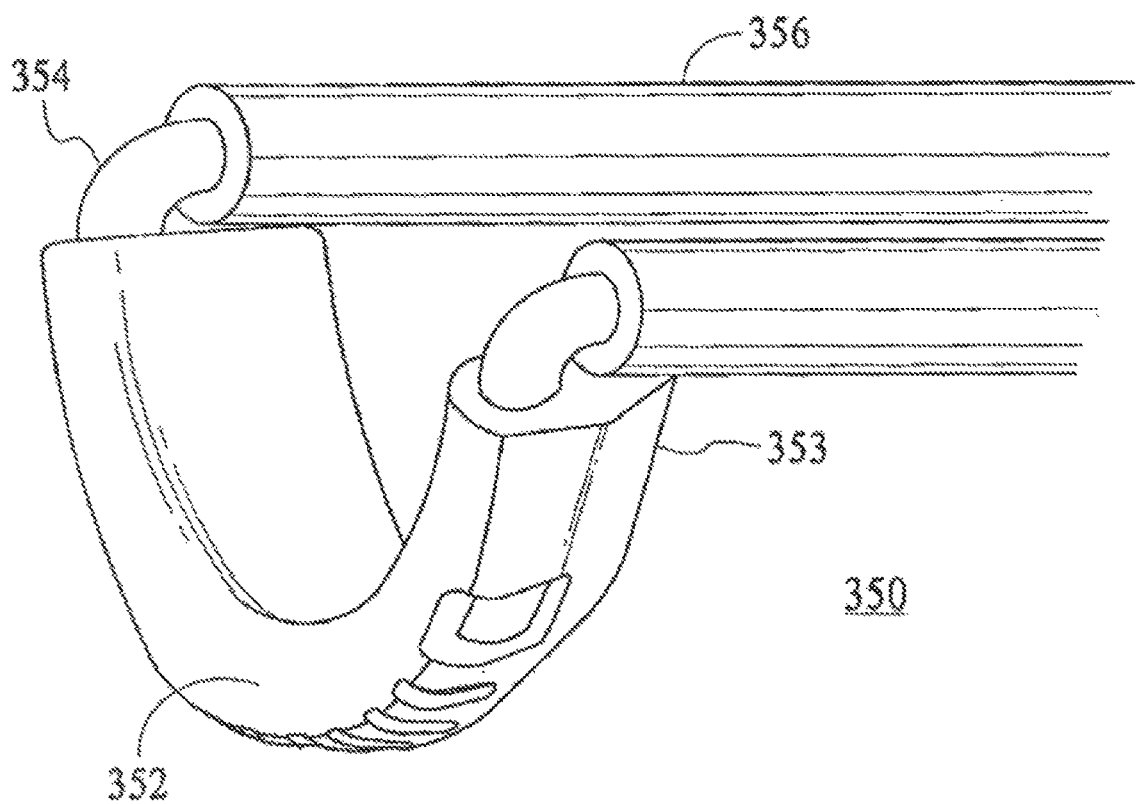
FIG. 11 is a representative schematic illustration of a wire loop for performing TURP in conjunction with the method and apparatus for C-LAP of the present invention.

In another method of using the system of the present invention, the C-LAP can be combined with a modified TURP procedure that uses a hot loop or wire resecting tool. FIG. 11 is a representative schematic illustration of a wire loop 350 for performing TURP in conjunction with the method and apparatus for C-LAP of the present invention. In this representative embodiment, the wire loop 350 has a resistive heating portion 352 with a beveled cutting edge 353. As current flows to the resistive heating portion 352 through wire feeds 354, heat is produced. Insulation 356 serves to protect and thermally and electrically insulate wire feeds 354 as the wire loop tool 350 is inserted through a lumen 302 of an endoscope or other access cannula.

Many of the lasers usable for the contact laser ablation procedure described herein produce a beneficial layer of tissue coagulation surrounding the areas where tissue has been vaporized. In addition, the laser source 100 can be operated at a power level below the tissue vaporization threshold to create a deeper layer of coagulated tissue, if desired. The laser treatment can then be followed by use of the loop or hot wire to scrape away additional tissue. This combined use of contact laser ablation and a modified TURP procedure is particularly useful for quickly debulking especially large prostate glands. Unlike the standard TURP procedure, this modified TURP procedure is virtually bloodless because of the tissue coagulation produced by the laser.

Unless defined otherwise, all technical and scientific terms used herein have the same meaning as commonly understood by one of ordinary skill in the art to which the present invention belongs. Although any methods and materials similar or equivalent to those described can be used in the practice or testing of the present invention, the preferred methods and materials are now described. All publications and patent documents referenced in the present invention are incorporated herein by reference.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true purview, spirit and scope of the invention.

We claim:

1. An apparatus for laser treatment of tissue, comprising:
a laser configured to produce an output beam;
an optical fiber having a proximal end and a distal end;
a connector configured to couple the output beam of the laser into the proximal end of the optical fiber;
a beam-emitting distal tip located proximate the distal end of the optical fiber;
an optical fiber protection system including an infrared detector configured to detect a magnitude of an infrared signal emitted from the proximal end of the optical fiber;
means for determining a rate of rise of the infrared signal emitted from the proximal end of the optical fiber;
the distal end of the optical fiber configured for insertion through a working channel of an endoscope;
a photodetector configured to detect visible light emitted from the proximal end of the optical fiber; and
means for preventing operation of the laser when the detected level of visible light emitted from the proximal end of the optical fiber is below a predetermined level indicating that the beam-emitting distal tip of the optical fiber is inside of an endoscope channel.

2. The apparatus of claim 1, further comprising:
means for preventing operation of the laser when the detected level of visible light emitted from the proximal end of the optical fiber is below a second predetermined level indicating potential damage in the optical fiber; and
means for indicating to a user that the optical fiber is potentially damaged.

3. The apparatus of claim 1, further comprising:
means for determining a rate of change of the visible light detected by the photodetector; and
means for preventing operation of the laser when the detected level of visible light emitted from the proximal end of the optical fiber drops below a predetermined level at a rate higher than a rate indicating that the beam-emitting distal tip of the optical fiber has been withdrawn into an endoscope channel.

4. The apparatus of claim 3, further comprising:
means for preventing operation of the laser when the detected level of visible light emitted from the proximal end of the optical fiber drops below a predetermined level at a rate higher than a rate indicating potential damage in the optical fiber; and
means for indicating to a user that the optical fiber is potentially damaged.

5. The apparatus of claim 1, further comprising means for modulating the visible light beam to indicate an operating condition of the apparatus.

6. The apparatus of claim 5, wherein the means for modulating the visible light beam flashes the visible light beam to indicate the operating condition of the apparatus.

7. The apparatus of claim 5, wherein the means for modulating the visible light beam changes a color of the visible light beam to indicate the operating condition of the apparatus.

* * * * *